US00PP34826P2

(12) United States Plant Patent
Lazzeri

(10) Patent No.: US PP34,826 P2
(45) Date of Patent: Dec. 13, 2022

(54) ***MANDEVILLA* PLANT NAMED 'LVDIP1601'**

(50) Latin Name: *Mandevilla hybrida*
Varietal Denomination: 'LVDIP1601'

(71) Applicant: Carlo Lazzeri, Vacaria (BR)

(72) Inventor: Carlo Lazzeri, Vacaria (BR)

( * ) Notice: Subject to any disclaimer, the term of this patent is extended or adjusted under 35 U.S.C. 154(b) by 0 days.

(21) Appl. No.: 17/829,260

(22) Filed: May 31, 2022

Related U.S. Application Data

(60) Provisional application No. 63/197,795, filed on Jun. 7, 2021.

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232, 226
CPC ... A01H 5/02; A01H 5/12; A01H 6/08; A01H 6/088
See application file for complete search history.

(56) References Cited

U.S. PATENT DOCUMENTS

PP19,399 P2 * 11/2008 Misato ..... A01H 6/088 Plt./232

* cited by examiner

*Primary Examiner* — June Hwu
(74) *Attorney, Agent, or Firm* — C. Anne Whealy

(57) ABSTRACT

A new and distinct cultivar of *Mandevilla* plant named 'LVDIP1601', characterized by its upright to outwardly spreading and trailing plant habit; moderately vigorous to vigorous growth habit; early and freely flowering habit; single bright pink-colored flowers; and good container performance.

2 Drawing Sheets

Figure 1:
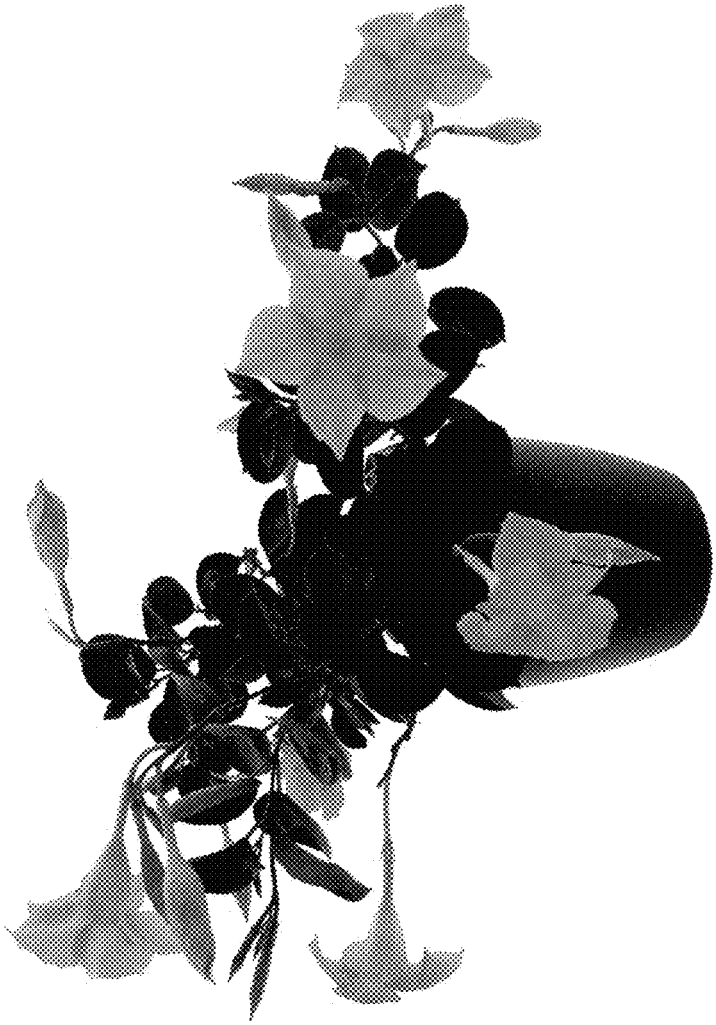

Botanical designation: *Mandevilla hybrida.*
Cultivar denomination: 'LVDIP1601'.

STATEMENT REGARDING PRIOR DISCLOSURES BY INVENTOR/APPLICANT

An European Plant Breeder's Rights application for the instant plant was filed by the Inventor/Applicant on Jun. 7, 2021, application number 2021/1461. Foreign priority is not claimed to this application.

BACKGROUND OF THE INVENTION

The present invention relates to a new and distinct cultivar of *Mandevilla* plant, botanically known as *Mandevilla hybrida* and hereinafter referred to by the name 'LVDIP1601'.

The new *Mandevilla* plant is a product of a planned breeding program conducted by the Inventor in Vacaria, Brazil. The objective of the breeding program is to develop new strong and freely flowering *Mandevilla* plants with attractive flowers and good garden performance.

The new *Mandevilla* plant originated from a cross-pollination in 2015 in Vacaria, Brazil of *Mandevilla hybrida* 'Sunparasuji' (trade name, Classic Red Star), disclosed in U.S. Plant Pat. No. 19,931, as the female, or seed, parent with *Mandevilla hybrida* 'Sunpararosta', disclosed in U.S. Plant Pat. No. 23,213, as the male, or pollen, parent. The new *Mandevilla* plant was discovered and selected by the Inventor as a single flowering plant from within the progeny of the stated cross-pollination grown in a controlled greenhouse environment in Vacaria, Brazil in November, 2016.

Asexual reproduction of the new *Mandevilla* plant by terminal stem cuttings in a controlled environment in Vacaria, Brazil since January, 2017 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LVDIP1601'. These characteristics in combination distinguish 'LVDIP1601' as a new and distinct *Mandevilla* plant:

1. Upright to outwardly spreading and trailing plant habit.
2. Moderately vigorous to vigorous growth habit.
3. Early and freely flowering habit.
4. Single bright pink-colored flowers.
5. Good container performance.

Plants of the new *Mandevilla* can be compared to plants of the female parent, 'Sunparasuji'. Plants of the new *Mandevilla* differ primarily from plants of 'Sunparasuji' in the following characteristics:

1. Plants of the new *Mandevilla* are not as vigorous as plants of 'Sunparasuji'.
2. Plants of the new *Mandevilla* have lighter green-colored leaves than plants of 'Sunparasuji'.
3. Plants of the new *Mandevilla* have bright pink-colored flowers whereas plants of 'Sunparasuji' have red-colored flowers with white-colored stripes.

Plants of the new *Mandevilla* can be compared to plants of the male parent, 'Sunpararosta'. Plants of the new *Mandevilla* differ primarily from plants of 'Sunpararosta' in the following characteristics:

1. Plants of the new *Mandevilla* are not as vigorous as plants of 'Sunpararosta'.
2. Plants of the new *Mandevilla* have bright pink-colored flowers whereas plants of 'Sunpararosta' have dark pink- colored flowers.

Plants of the new *Mandevilla* can also be compared to plants of *Mandevilla hybrida* 'Sunparaprero', disclosed in U.S. Plant Pat. No. 19,399. In side-by-side comparisons, plants of the new *Mandevilla* differ primarily from plants 'Sunparaprero' in the following characteristics:

1. Plants of the new *Mandevilla* are not as trailing as plants of 'Sunparaprero'.
2. Plants of the new *Mandevilla* have bright pink-colored flowers whereas plants of 'Sunparaprero' have dark pink- colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'LVDIP1601' grown in a container.

Figure 2:
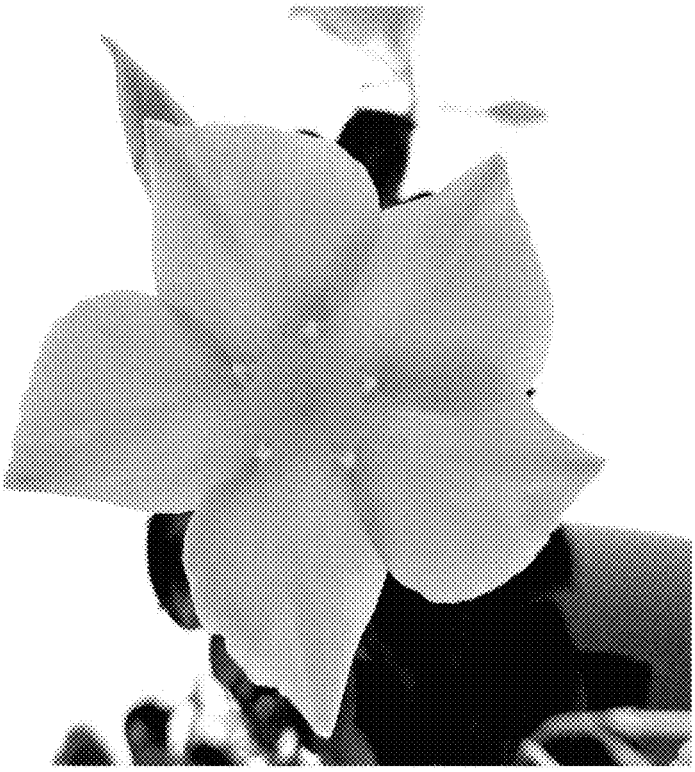

The photograph on the second sheet (FIG. 2) is a close-up view of a typical flower of 'LVDIP1601'.

DETAILED BOTANICAL DESCRIPTION

The aforementioned photographs and following observations, measurements and values describe plants grown during the summer in 10.5-cm containers in a polyethylene-covered greenhouse in Merano, Italy and under cultural practices typical of commercial *Mandevilla* production. During the production of the plants, day temperatures ranged from 20° C. to 28° C. and night temperatures ranged from 10° C. to 18° C. Plants were 20 weeks old when the photographs and description were taken. In the following description, color references are made to The Royal Horticultural Society Colour Chart, 2015 Edition, except where general terms of ordinary dictionary significance are used.

Botanical classification: *Mandevilla hybrida* 'LVDIP1601'.

Parentage:

*Female, or seed, parent.*—*Mandevilla hybrida* 'Sunparasuji', disclosed in U.S. Plant Pat. No. 19,931.

*Male, or pollen, parent.*—*Mandevilla hybrida* 'Sunpararosta', disclosed in U.S. Plant Pat. No. 23,213.

Propagation:

*Type*.—By vegetative cuttings.

*Time to initiate roots, summer*.—About three weeks at temperatures about 25° C.

*Time to initiate roots, winter*.—About four weeks at temperatures about 14° C.

*Time to produce a rooted young plant, summer*.—About five weeks at temperatures about 25° C.

*Time to produce a rooted young plant, winter*.—About six weeks at temperature about 14° C.

*Root description*.—Thin, fibrous; typically creamy white in color, actual color of the roots is dependent on substrate composition, water quality, fertilizers, substrate temperature and physiological age of roots.

*Rooting habit*.—Freely branching; medium density.

Plant description:

*Plant and growth habit*.—Upright to outwardly spreading and trailing plant habit; roughly broadly obovate in overall shape; moderately vigorous to vigorous growth habit and moderate growth rate.

*Plant height, soil level to top of foliar plane*.—About 18.9 cm.

*Plant height, soil level to top of floral plane*.—About 23.5 cm.

*Plant diameter* (*spread*).—About 44.3 cm.

*Lateral branch description*.—Branching habit: Freely branching habit, typically about three primary lateral branches each with about two secondary lateral branches. Length: About 18.1 cm. Diameter: About 2.5 mm. Internode length: About 2.6 cm. Aspect: Primary lateral branches, mostly upright; secondary lateral branches, about 25° to 45° from primary branch axis. Strength: Strong. Texture and luster: Smooth, glabrous; slightly glossy; becoming woody with development. Color, developing and developed: Close to a blend of 143B and 143C; when woody, close to 199A.

Leaf description:

*Arrangement*.—Opposite, simple.

*Length*.—About 5.3 cm.

*Width*.—About 4.1 cm.

*Shape*.—Broadly ovate to broadly elliptic.

*Apex*.—Apiculate to abruptly acute.

*Base*.—Truncate to shallowly cordate.

*Margin*.—Entire.

*Texture and luster, upper and lower surfaces*.—Smooth, glabrous; moderately coriaceous; moderately glossy.

*Venation pattern*.—Pinnate.

*Color*.—Developing leaves, upper surface: Close to 143A. Developing leaves, lower surface: Close to 177A. Full expanded leaves, upper surface: Slightly darker than a blend of NN137A and 147A; venation, close to NN144C. Fully expanded leaves, lower surface: Close to 146B; venation, close to 145C to 145D.

*Petioles*.—Length: About 1 cm. Diameter: About 2 mm by 2 mm. Strength: Moderately strong. Texture and luster, upper surface: Smooth, glabrous; moderately glossy. Texture and luster, lower surface: Smooth, glabrous; slightly glossy. Color, upper surface: Close to 144A. Color, lower surface: Close to 144C.

Flower description:

*Flower type and flowering habit*.—Single salverform flowers arranged in terminal and axillary cymes; flowers face outwardly to slightly upright or slightly nodding; freely flowering habit with about seven flowers per inflorescence and about 90 flower buds and open flowers developing per plant during the flowering season.

*Natural flowering season*.—Plants flower continuously from spring into the autumn in Italy; plants begin flowering about 45 days after planting rooted young plants.

*Flower longevity on the plant*.—Individual flowers last about ten days; flowers not persistent.

*Fragrance*.—None detected.

*Inflorescence height*.—About 14.9 cm.

*Inflorescence diameter*.—About 9.5 cm.

*Flower buds*.—Length: About 5.6 cm. Diameter: About 9 mm. Shape: Narrowly oblanceolate. Texture and luster: Smooth, glabrous; slightly glossy. Color: Distally, close to 54A; mid-section, close to 54C; proximally, close to 145C and tube, close to 145A.

*Flowers*.—Appearance: Flared trumpet, corolla fused and five-parted. Diameter: About 6.8 cm by 6.8 cm. Depth (length): About 6.7 cm. Throat diameter: About 1.5 cm. Tube length: About 5.1 cm. Tube diameter: Proximally, about 4 5 mm; distally, about 1.7 cm.

*Corolla*.—Quantity and arrangement: Five petals arranged in a single whorl; lower 60% portion (approximately) of the petals are fused into a funnel-form tube. Petal lobe length: About 3.3 cm. Petal lobe width: About 2.8 cm. Petal shape and appearance: Roughly unequal spatulate; slightly convex and moderately reflexed. Petal apex: Short apiculate, unequal. Petal margin: Entire; moderately undulate. Petal texture and luster, upper surface: Smooth, glabrous; velvety; slightly glossy. Petal texture and luster, lower surface: Smooth, glabrous; slightly velvety; slightly glossy. Throat texture: Smooth, glabrous; velvety. Tube texture: Smooth, glabrous; slightly velvety. Color: Petal, when opening, upper surface: Close to N57A; towards the throat, close to 61D. Petal, when opening, lower surface: Close to 58B; at the apex, tinged with close to N155A; towards the base, close to 63C. Petal, fully opened, upper surface: Close to 63B; towards the margins, close to 63B to 63C; venation, similar to lamina color; with subsequent development, color becoming closer to 63C and towards the margins, close to 65A. Petal, fully opened, lower surface: Close to 64D; central band, close to 65A; flushed and tinged with close to N155C; midvein, close to 65A; with subsequent development, color becoming closer to 63C and towards the margins, close to 65A and flushed with close to N155A. Throat: Close to 23A; at the base of the throat, close to 151C; venation, similar to lamina colors. Tube: Distally, close to 54C and proximally, close to a blend of 145D and 150D; at the base, close to 145A; venation, similar to lamina colors.

*Sepals*.—Quantity and arrangement: Five sepals arranged in a single whorl. Length: About 7 mm. Width: About 1 mm. Shape: Lanceolate. Apex: Narrowly acuminate. Base: Broadly cuneate and fused. Margin: Entire. Texture and luster, upper surface: Smooth, glabrous; moderately glossy. Texture and luster, lower surface: Smooth, glabrous; matte. Color: When developing and fully developed, upper surface: Close to 145C; towards the base, close to 145A. When developing and fully developed, lower surface: Close to 145B; towards the base, close to 145A.

*Peduncles*.—Length: About 9.7 cm. Diameter: About 2 mm. Strength: Strong. Aspect: About 20° from lateral branch axis. Texture and luster: Smooth, glabrous; moderately glossy. Color: Close to 143B.

*Pedicels*.—Length: About 1.6 cm. Diameter: About 2 mm. Strength: Strong. Aspect: About 20° to 60° from peduncle axis. Texture and luster: Smooth, glabrous; moderately glossy. Color: Close to 145A.

*Reproductive organs*.—Stamens: Quantity and arrangement: Typically five; basifixed; anthers connivent. Filament length: About 2 mm. Filament color: Close to 150D. Anther shape: Narrowly oblong. Anther size: About 1.5 mm by 9 mm. Anther color: Close to 162D. Pollen amount: None observed. Pistils: Quantity: Typically one. Pistil length: About 2.6 cm. Style length: About 2.3 cm. Style color: Close to 145C. Stigma diameter: About 1.75 mm. Stigma shape: Club-shaped, pointed. Stigma color: Close to 147D. Ovary color: Close to 144A.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5° C. to about 40° C. and to be suitable for USDA Hardiness Zones 9 to 13.

It is claimed:

1. A new and distinct *Mandevilla* plant named 'LVDIP1601' as illustrated and described.

* * * * *